US007001762B1

(12) United States Patent
Giuseppe et al.

(10) Patent No.: US 7,001,762 B1
(45) Date of Patent: Feb. 21, 2006

(54) **ISOLATION AND CHARACTERIZATION OF A *N. CRASSA* SILENCING GENE AND USES THEREOF**

(75) Inventors: Macino Giuseppe, Rome (IT); Cogoni Carlo, Rome (IT)

(73) Assignee: Universita degli Studi di Roma "La Sapienza", (IT)

( * ) Notice: Subject to any disclaimer, the term of this patent is extended or adjusted under 35 U.S.C. 154(b) by 0 days.

(21) Appl. No.: 09/913,878

(22) PCT Filed: Feb. 16, 2000

(86) PCT No.: PCT/IT00/00048

§ 371 (c)(1),
(2), (4) Date: Jan. 23, 2002

(87) PCT Pub. No.: WO00/50581

PCT Pub. Date: Aug. 31, 2000

(30) Foreign Application Priority Data

Feb. 22, 1999 (IT) .............................. RM99A0117

(51) Int. Cl.
*C12N 15/63* (2006.01)
(52) U.S. Cl. ................. 435/320.1; 435/325; 435/252.3; 435/254.11; 435/419
(58) Field of Classification Search ............... 536/23.1; 435/320.1, 252.3, 254.11
See application file for complete search history.

(56) References Cited

OTHER PUBLICATIONS

Everett et al. Nature Genetics, 1997, vol. 17, pp. 411-421.*
Scott et al. Nature Genetcs, 1999, vol. 21, pp. 440-443.*
47.2% identity in 439 aa overlap with amino acids 897-1330 of SeqIdNo. 3 & Database Genesq EBI, Hinxton, U.K. (1998).
Linden, H. et al., "White collar 2, a partner in blue-light signal transduction, controlling expression of light-regulated genes in *Neurospora crassa*", EMBO Journal, vol. 16, No. 1, pp. 98-100 (1997).
Cogoni et al., "Posttranscriptional gene silencing in *Neurospora* by a RecQ DNA helicase", SCIENCE, vol. 286, No. 5448, pp. 2342-2344 (1999).
Reeck, G. et al., "'Homology' in Proteins and Nucleic Acids: A Terminology Muddle and a Way out of It", CELL, vol. 50 pp. 667 (1987).
Tabara et al., "The rde-1 gene, RNA interference and transposon silencing in *C. elegans*", CELL, vol. 99 pp. 123-132 (1999).
Cottage, A., "Hypothetical 114.9kDa protein t22b3.2", Database Swissprot 'Online! EBI (1996).
Catalanotto et al., "Gene silencing in worms and fungi", Nature, vol. 404, pp. 245 (2000).
Sherman J.M., et al., "An Uncertain Silence", Trends in Genetics, NL, Elsevier Science Publishers, vol. 13, n. 8, pp. 308-313, (1997).
Cogoni, "*Neurospora crassa* qde-1 gene, partial", EMBL Sequence Database, (1999).
Cogoni et al., "RNA-dependent RNA polymerase (fragment", EMBL Sequence Database, (1999).
Cogoni et al., "Gene Silencing in *Neurospora crassa* requires a protein homologous to RNA-dependent RNA polymerase", Nature, vol. 399, pp. 166-169 (1999).
Cogoni et al., "Isolation of quelling-defective (qde) mutants impaired in posttranscriptional transgene-induced gene silencing in *Neurospora crassa*", Proc. Nat. Acad. Sci. U.S.A., vol. 94, pp. 10233-10238, (1997).
Cogoni et al., "Quelling: transgene-induced gene silencing in *Neurospora crassa*", NATO Advanced Science Institutes, Series H: Cell Biology, vol. 104, pp. 103-112, (1998).

* cited by examiner

*Primary Examiner*—Celian Qian
(74) *Attorney, Agent, or Firm*—Gauthier & Connors LLP

(57) ABSTRACT

A nucleotide sequence encoding for a protein characterized in that it has a silencing activity and comprises a RNA-dependent RNA polymerase domain is disclosed; furthermore expression vectors suitable for the expression of said sequence in bacteria, plants, animals and fungi are disclosed; the invention refers also to organisms transformed by such vectors.

7 Claims, 5 Drawing Sheets

FIG. 1

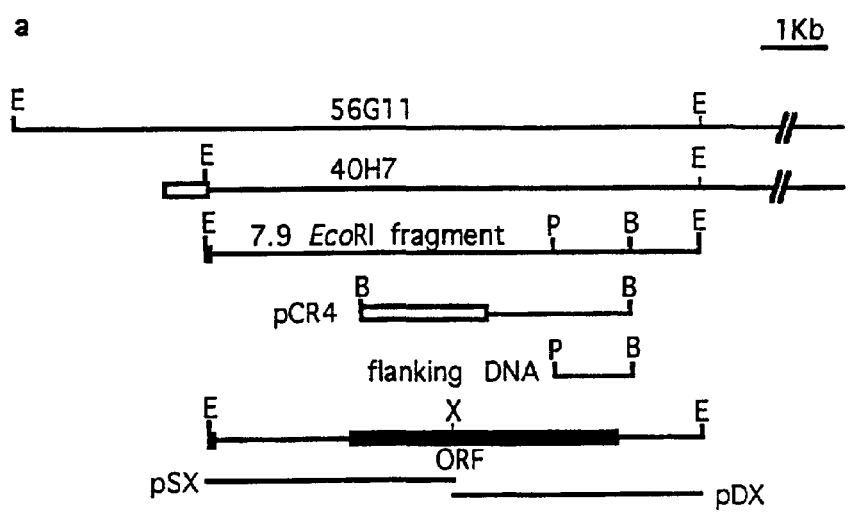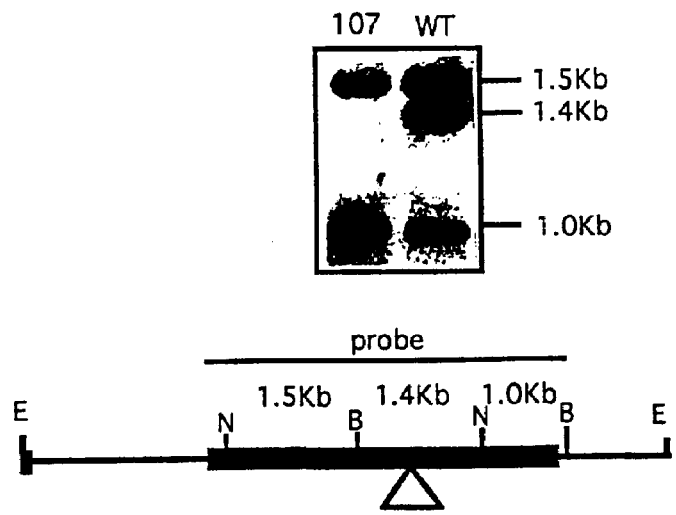
FIG. 2

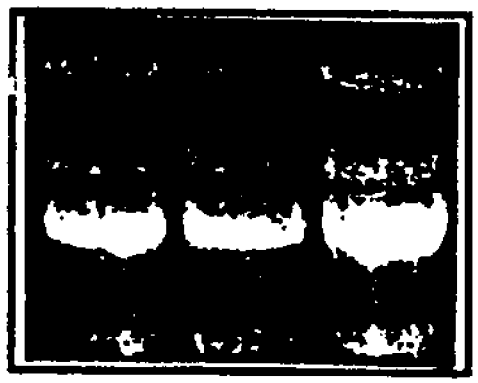
FIG. 3

```
MNPITPRKRN SPVEEIINRL NNDYNLGLQC VADTTLTPHR RKELAESDED FGRHDKIYRA    60
LNFLYWRKDD SLNQAEANFF IEAKAASSNW VPKAHADPDT LPWSKEPPRA ATAGQQWALQ   120
TVLLEVLNRF MPPPNNTPGR TFGRTLSGPS GLSRPTSTNT KRKDEPANVT FADPPKRSLT   180
RSATGPPIHG AAIPLKFPDP VNTGSKRPSL ESENLNQCTK RAKGKLSDNV AAAAAPPVPI   240
ASALDKVPTR RHANTRDPTA TGHRRADQVD SFDTSQGTSY GSSVFSACRH NQSTTQSSFE   300
APPSQPREKR PVDATVFEAG HLIESPSKGR TTKSHIDNQP LSSSSQGETS FSTYYESFPS   360
SGGEGAIPEP SRSNGLARSE ESARSQVQVH APVVAARLRN IWPKFPKWLH EAPLAVAWEV   420
TRLFMHCKVD LEDESLGLKY DPSWSTARDV TDIWKTLYRL DAFRGKPFPE KPPNDVFVTA   480
MTGNFESKGS AVVLSAVLDY NPDNSPTAPL YLVKLKPLMF EQGCRLTRRF GPDRFFEILI   540
PSPTSTSPSV PPVVSKQPGA VEEVIQWLTM GQHSLVGRQW RAFFAKDAGY RKPLREFQLR   600
AEDPKPIIKE RVHFFAETGI TFRPDVFKTR SVVPAEEPVE QRTEFKVSQM LDWLLQLDNN   660
TWQPHLKLFS RIQLGLSKTY AIMTLEPHQI RHHKTDLLSP SGTGEVMNDG VGPMSRSVAK   720
RIRDVLGLGD VPSAVQGRFG SAKGMWVIDV DDTGDEDWIE TYPSQRKWEC DFVDKHQRTL   780
EVRSVASELK SAGLNLQLLP VLEDRARDKV KMRQAIGDRL INDLQRQFSE QKHALNRPVE   840
FRQWVYESYS SPATRVSHGR VPFLAGLPDS QEETLNFLMN SGFDPKKQKY LQDIAWDLQK   900
RKCDTLKSKL NIRVGRSAYI YMIADFWGVL EENEVHVGFS SKFRDEEESF TLLSDCDVLV   960
ARSPAHFPSD IQRVRAVFKP ELHSLKDVII FSTKGDVPLA KKLSGGDYDG DMAWVCWDPE  1020
IVDGFVNAEM PLEPDLSRYL KKDKTTFKQL MASHGTGSAA KEQTTYDMIQ KSFHFALQPN  1080
FLGMCTNYKE RLCYINNSVS NKPAIILSSL VGNLVDQSKQ GIVFNEASWA QLRRELLGGA  1140
LSLPDPMYKS DSWLGRGEPT HIIDYLKFSI ARPAIDKELE AFHNAMKAAK DTEDGAHFWD  1200
PDLASYYTFF KEISDKSRSS ALLFTTLKNR IGEVEKEYGR LVKNKEMRDS KDPYPVRVNQ  1260
VYEKWCAITP EAMDKSGANY DSKVIRLLEL SFLADREMNT WALLRASTAF KLYYHKSPKF  1320
VWQMAGRQLA YIKAQMTSRP GEGAPALMTA FMYAGLMPDK KFTKQYVARL EGDGSEYPDP  1380
EVYEVLGDDD FDGIGFTGNG DY
```

ISOLATION AND CHARACTERIZATION OF A *N. CRASSA* SILENCING GENE AND USES THEREOF

BACKGROUND OF THE INVENTION

1. Field of the Invention

The present invention relates to the isolation and characterization of a *Neurospora crassa* gene encoding for an essential activity in the co-suppression process and to uses and applications thereof in vegetal, animal and fungine fields.

2. Description of the Prior Art

The production of transgenic organisms is of large utility both in basic and applied biological research. The transgenic DNA is usually integrated in the genome and transferred as a Mendelian character. However, in various instances, the transgene introduction induces gene silencing phenomena (Flavell, R. B. 1994), i.e. the repression of the expression of the transgene itself and/or of one or more endogenous homologous genes.

The gene silencing can act at two levels: transcriptional (trans-inactivation) where transgenes contain sequences homologous to the silenced gene promoter (Vaucheret, 1993); and post-transcriptional (co-suppression) which requires homologies between coding regions (Flavell, 1994; Stam et al., 1997; Baulcombe, 1996).

Generally the silencing induced by a transgene requires an almost complete sequence homology (from 70% to 100%) between transgene and silenced gene sequences (Elkind, 1990).

In the *Neurospora crassa* filamentous fungus, during the vegetative phase, the presence of transgenes induces a post-transcriptional gene silencing phenomenon, named "quelling" (Cogoni et al., 1996).

By using the al-1 gene (albino 1) (Schmidhauser et al., 1990) as silencing visual marker, many features of the phenomenon have been discovered (Cogoni et al., 1996). Particularly the al-1 gene "quelling" in *Neurospora* is characterized in that: 1) the gene silencing is reversible further to the loss of transgene copies; 2) the reduction of mRNA basal level results from a post-transcriptional effect; 3) transgenes containing at least a region of 132 base pairs which is identical to the region encoding for the target gene are sufficient to induce the "quelling"; 4) the duplication of promoter sequences is ineffective to induce the silencing; 5) the "quelling" exhibits a dominant behavior in eterocarions containing both transgenic and untransformed nuclei, indicating the involvement of a molecule which is acts "in trans" among the nuclei; 6) the expression of an aberrant RNA transcribed by the transgenic locus is strictly correlated to silencing, suggesting that the "quelling" can be induced and/or mediated by a transgenic RNA molecule.

Therefore homologies between *Neurospora* silencing and plant co-suppression can be pointed out. The gene silencing in *Neurospora* is reversible, as result of transgenic copies instability during mitotic phase; in plants also the co-suppression reversion is associated with the reduction of transgene copy number, resulting from intra-chromosomal recombination during mitosis or meiosis (Mittelstein Scheid et al., 1994; Stam et al., 1997). Thus both in plants and in *Neurospora* the transgene presence is required to maintain the silencing. As in *Neurospora*, a decrease of the mRNA basal level of the silenced gene results from a post-transcriptional mechanism (Dehio and Schell 1994; van Blokand et al., 1994; de Carvalho et al., 1995). Furthermore to induce the "quelling", transgenes must contain a portion of the silencing target gene coding sequence, being the promoter region ineffective. In plants coding regions with no promoter sequences can induce silencing (van Blokand et al., 1994) and, as in the "quelling", promoters or functionally active gene products are not required for the co-suppression.

One of the similarities between "quelling" and co-suppression in plants is that both mechanisms are mediated by diffusion factors. In *Neurospora* eterokaryotic strains, nuclei wherein the albino-1 gene is silenced are able to induce the al-1 gene silencing of the other not transformed nuclei, all sharing the same cytoplasmic environment (Cogoni et al., 1996). In plants the presence of a diffusion factor results from the fact that the co-suppression is effective in inhibiting the replication of Tobacco Etch Virus (TEV), a RNA virus with an exclusively cytoplasmic cycle. The occurrence of highly diffusible factors, which are effective to mediate the co-suppression, has been demonstrated using the grafting technique in tobacco (Palaqui et al., 1997), showing that silenced tobacco plants are able to transfer the silencing to non-silenced plants through grafting.

The fact that "quelling" and co-suppression share all these features suggests that mechanisms involved in post-transcriptional gene silencing in plants and in fungi can be evolved by an ancestral common mechanism.

Recently gene inactivation phenomena resulting from transgene introduction have been disclosed in animals. In *Drosophila melanogaster* the location of a transgene close to heterochromatic centers results in a variegate expression (Wallrath and Elgin, 1995; Pirrotta, V., 1997). Similar expression profiles have been observed when the reference transgene is within tandem arrayed transposons, indicating that tandem repeats are effective to induce the chromatin condensation. (Dorer and Henikoff, 1994). Again in *Drosophila* Pal-Bhadra et al. (1997) have observed that the transgene introduction can lead to gene inactivation phenomena, similar to the co-suppression.

Gene silencing phenomena resulting from transegene sequence repeats have been disclosed recently in mammalians.

Garrick et al. (1998) produced mouse transgenic lines wherein 100 transgenic copies are present only in a locus and are directly tandem arrayed. The transgene expression has been disclosed to be inversely proportional to the number of occurring copies, indicating that silencing phenomena dependent on repeat copies are present also in mammalians.

BRIEF SUMMARY OF THE INVENTION

Therefore the identification of *Neurospora* genes which are involved in the silencing is the first step to modulate the same process in plants, animals and fungi. The silencing modulation is of great relevance when transgenic organisms able to express the desired phenotype are produced.

The authors of the present invention have already isolated *Neurospora crassa* strains having mutations regarding essential functions for gene silencing mechanism (Cogoni and Macino, 1997); 15 independent isolated mutants define three complementation groups, thus identifying the qde-1, qde-2 and qde-3 genes (qde stands for "quelling"-deficient), whose products are essential to the silencing machinery. qde genes are essential to the *Neurospora* silencing, as suggested by the fact that silencing of three independent genes (al-1, al-2 and qa-2) is impaired by qde mutations (Cogoni and Macino, 1997).

The authors of the invention have identified and cloned now one out of *Neurospora* qde genes, the qde-1 gene, thus identifying one of required factors for silencing. By considering the similarity between "quelling" and co-suppression, genes orthologous to the isolated gene are involved in co-suppression and more generally in gene silencing in other organisms, like plants, fungi and animals.

The present invention can be applied with reference to two general scope: 1) silencing potentiation as a tool for inactivating more effectively and durably a desired gene, and 2) silencing suppression to obtain a better expression of the introduced transgenes.

As to the silencing potentiation, the over-expression of one or more genes controlling the phenomenon can lead to higher efficiency and/or stability thereof. Therefore the introduction of qde-1 gene or of homologous genes thereof in microorganisms can constitute a tool to repress more effectively gene functions. Particularly this approach is specially useful in plants wherein the co-suppression is usually used for the "knock-out" of gene functions. In plants again the gene silencing potentiation can be used to obtain lines resistant to pathogen virus, by introducing transgenes encoding for viral sequences, in order to achieve the expression inhibition of the virus itself (Flavell et al., 1994).

Analogous applications are suitable for animals, wherein some indications suggest that silencing can inhibit the suitable expression of introduced transgenes (Garrick et al., 1998).

On the contrary, there are instances wherein it is desirable not to have or to reduce the gene silencing, i.e. where a transgene is to be over-expressed. It is known that the co-suppression is strictly correlated both with the presence of an high copy number of the transgene, and with a transgene high expression. This correlation can hamper the production of transgenic organisms which express a transgene at high levels, because more high is the expression and/or the copy number, more probable is to evoke silencing responses. As above mentioned, analogous mechanisms of gene inactivation, dependent on a high copy number, have been disclosed in animals. In these circumstances plant or animal lines, totally or partially ineffective for silencing, constitute an ideal recipient wherein the desired gene can be over-expressed. The invention can be applied within this scope using different approaches:

A) Identification and production of mutant lines in genes homologous to qde-1 gene, in plants, animals and fungi.

The knowledge of *Neurospora* qde-1 gene, essential for silencing mechanism, can allow the isolation of mutant lines in other organisms, mutated in genes homologous to qde-1. For example by means of amplifications using degenerated primers, designed from the most conserved regions of qde-1 gene, mutant lines in homologous genes can be identified, by analysis of insertion mutant gene banks, already available for many plant species. Both in fungi and animals such mutants can be obtained, following the identification of the homologous gene, by means of "gene disruption" techniques using homologous recombination.

B) Reduction of qde-1 gene expression

Other strategies for the production of silencing-deficient lines comprise the use of *Neurospora* qde-1 gene or homologous genes thereof. qde-1 or homologous genes can be introduced into suitable expression vectors to express them in an anti-sense orientation in order to inhibit the expression of resident endogenous genes. Alternatively portions of qde-1 or of homologous genes can be over-expressed, in order to obtain a negative dominant effect and thus blocking the function of qde-1 endogenous genes.

The authors of the present invention have cloned and characterised the *Neurospora crassa* qde-1 gene. The sequence analysis of the qde-1 gene detected a region having a significant homology with a RNA-dependent RNA polymerase, isolated from tomato, which was suggested, but not demonstrated, to be involved in the co-suppression mechanism (Schiebel et al., 1998).

The authors of the invention for the first time have demonstrated that a gene encoding for a RNA-dependent RNA polymerase is involved in gene silencing induced by transgenes. Therefore for the first time it is disclosed that a gene belonging to the RNA-dependent RNA polymerase family is an essential component also for inactivation mechanism of the repeat sequences.

Within the scope of the invention the reference to homology percent means similarity percent, i.e. number of identical residues+number of conserved residues with respect to the total residues of the considered sequence.

Therefore it an object of the present invention a nucleotide sequence encoding for a protein characterized in having a silencing activity and in comprising a RNA dependent RNA polymerase domain, wherein the domain is at least 30% homologous with the amino acid sequence from aa. 710 to aa. 1282 of SEQ ID No. 1. Preferably the domain is at least 40% homologous with the amino acid sequence from aa. 710 to aa. 1282 of SEQ ID No. 1. More preferably the domain is at least 50% homologous with the amino acid sequence from aa. 710 to aa. 1282 of SEQ ID No. 1. Most preferably the domain comprises the amino acid sequence from aa. 710 to aa. 1282 of SEQ ID No. 1. According to a particular embodiment the nucleotide sequence encodes for a protein having the amino acid sequence of SEQ ID No. 1 or functional portions thereof. Even more preferably the nucleotide sequence is the nucleotide sequence of SEQ ID No. 1 or its complementary sequence.

A further object of the invention is an expression vector comprising, under the control of a promoter which is expressed in bacteria, the nucleotide sequence of the invention. Those skilled in the art will appreciate that any plasmid suitable for a correct and effective expression of the protein of the expression in bacteria can be used and it is within the scope of the invention.

A further object of the invention is an expression vector comprising, under the control of a promoter which is expressed in plants or in specific plant organs, the nucleotide sequence of the invention, both in a sense and anti-sense orientation. Those skilled in the art will appreciate that any plasmid suitable for a correct and effective expression of the protein of the invention in plants or in specific plant organs can be used and it is within the scope of the invention.

A further object of the invention is an expression vector comprising, under the control of a promoter which is expressed in fungi, the nucleotide sequence of the invention, both in a sense and anti-sense orientation. Those skilled in the art will appreciate that any plasmid suitable for a correct and effective expression of the inventive protein in fungi can be used and it is within the scope of the invention.

A further object of the invention is an expression vector comprising, under the control of a promoter which is expressed in animals, the nucleotide sequence of the invention, both in a sense and anti-sense orientation. Those skilled in the art will appreciate that any plasmid suitable for a correct and effective expression of the protein of the invention in animals can be used and it is within the scope of the invention.

A further object of the invention is a prokaryotic organism transformed by using the expression vector active in bacteria of the invention.

A further object of the invention is a plant or a specific plant organ transformed by using the expression vector active in plants of the invention.

A further object of the invention is a plant mutated at the nucleotide sequence of the invention having a reduced or inhibited silencing activity.

A further object of the invention is a fungus transformed with the expression vector of the invention active in fungi.

A further object of the invention is a fungus mutated at the nucleotide sequence of the invention and having reduced or inhibited silencing activity.

A further object of the invention is a non-human animal transformed with the expression vector of the invention active in animals.

A further object of the invention is a non-human animal mutated at the nucleotide sequence of the invention and having a reduced or inhibited silencing activity.

A further object of the invention is a non-human animal mutated at the nucleotide sequence of the invention and having reduced or inhibited silencing activity.

A further object of the invention refers to a protein characterized in having a silencing activity and in comprising a RNA-dependent RNA polimerase domain, wherein the domain is at least 30% homologous with the amino acid sequence from aa. 710 to aa. 1282 of SEQ ID No. 1. Preferably the domain is at least 40% homologous with the amino acid sequence from aa. 710 to aa. 1282 of SEQ ID No. 1. More preferably the domain is at least 50% homologous with the amino acid sequence from aa. 710 to aa. 1282 of SEQ ID No. 1. Most preferably the domain comprises the amino acid sequence from aa. 710 to aa. 1282 of SEQ ID No. 1. According to a particular embodiment the nucleotide sequence encodes for a protein having the amino acid sequence of SEQ ID No. 1 or functional portions thereof.

It is within the scope of the present invention the use of the nucleotide sequence of the invention to modulate gene silencing in plants, animals and fungi.

The present invention now will be disclosed by way of non limiting examples with reference to the following figures:

BRIEF DESCRIPTION OF THE FIGURES

FIG. 1 shows the restoration of the al-1 expression in 107 insertional mutant strain. The total RNA has been extracted from mycetes collected after light induction over ten minutes from an al-1 silenced strain (6XW), a untransformed wild type strain (WT) and 107 mutant strain. For the hybridization an al-1 specific probe was used. In the lower part the restoration using an al-1 specific probe is showed.

FIG. 2 shows the genomic organization of the qde-1 gene. a) The two cosmides (56G11 and 40H7) able to complement the qde-1 mutants are represented. The white box in the 40H7 cosmid represents the sequences of the cosmid vector. A restriction map of 7,9 Kb qde-1 containing fragment obtained from 40H7 using EcoRi is showed: E(EcoRI), P(Pstl), B(BgIII). The black box represents the ORF identified within EcoRI 7,9 Kb fragment. The pDX and pSX plasmids containing the DNA fragments subcloned in the XbaI (X) and EcoRI (E) sites are also showed. B) Southern analysis of the 107 and WT strains. The genomic DNA was digested using BgII and NaeI. In the lower diagram the DNA probe used for the hybridization and the expected BgII/NaeI (B/N) restriction fragments are reported. The triangle represents the integration site in the 107 strain which determines the disappearance of the 1,0 Kb restriction fragment.

FIG. 3 represents the expression of the qde-1 gene in the 107 insertional mutant strain, untransformed wild type (WT) strain and al-1 silenced strain (6XW). The total RNA was hybridizated using a qde-1 specific probe. In the lower part the amount of gel loaded RNA is showed.

FIG. 4 represents the amino acid sequence deduced from the qde-1 gene. The underlining indicates the RdRP conserved domain as showed in the alignment of FIG. 5.

FIG. 5 represents a sequence alignment of the QDE-1 protein (SEQ ID No. 2) with other polypeptides from SwissProtein sequence database: ORF from Z488334 (eleg1) C. elegans, ORF from Z98533 (pom) S. pombe, ORF from AF080120 (araB) A. thaliana and RNA-dependent RNA polymerase from Y104403 (RdRP) tomato. Identical residues are pointed out in black, whereas the conservative replacements are showed in gray.

MATERIALS AND METHODS

Strains, Growing and Transforming Conditions

The methodology and heterokaryon analysis in Neurospora crassa substantially was the same as described in (Davis and De Sevres, 1970). The spheroplasts are prepared according to method of Vollmer and Yasnofsky (1997). The 107 strain was isolated in the following way: a qde-1 silenced strain, called 6xw, already described (Cogoni and Macino, 1997), was transformed with pMXY2 which contains the benomyl resistant beta-tubulin gene, which acts as dominant selectable marker in N. Crassa (Staben et al. 1989). Transformed strains able to grow in the presence of benilate containing medium were selected on the base of the carotenoid biosynthesis by visualization of the conidium colors: the conidia from the wild type strains were bright orange, whereas those from transformed strains having colors from white to yellow were indicative of a silencing activity.

Plasmids and Gene Libraries

The genomic gene qde-1 was isolated from a N. Crassa gene library in cosmides (Cabibbo et al., 1991). The sub-cloning of the restriction fragments from the gene library clones was carried out in the pBSK plasmid. Therefore the sub-clones were used in co-transforming experiments using pMXY2 or pES200 (containing the hygromycin resistant gene).

Southern and Northern Hybridizations

Chromosomal DNA was prepared according to Morelli et al. (1993). After digestion, the genomic DNA was transferred according to Maniatis et al. (1982). The probes were labeled by casual priming (Boheringer). The RNA was electrophoresed on agarose gel, transferred and blotted on Hybond N membranes.

DNA Analysis and Sequencing

The qde-1 nucleotide sequence was determined for both strands using TAQ FS polymerase and the fluorescence method and analyzed using an Applied Biosystems 373A automated apparatus; the nucleotide and amino acid derived sequences were analyzed by means of MacMolly Tetra program. A protein comparison was carried out using the BLASTP method. The ClustalW algorithm was used for the alignment.

Results

In order to clone the qde genes an insertional mutagenesis on an al-1 transgenic strain (6XW) which shows an albino phenotype (white) resulting from a post-transcriptional silencing of the al-1 endogenous gene was used: out of 100.000 independent transformed insertional strains, a strain (107) showed a reversion of the gene silencing visible as restoration of a bright orange wild type phenotype. The bright orange wild type phenotype of the 107 strain results from the restoration of the expression of al-1 mRNA, as demonstrated by a Northern analysis (see FIG. 1). Furthermore an heterokaryon assay revealed the mutation to be recessive and trans acting. In addition by means of the heterokaryon assay it was possible to establish that the 107 strain mutant belongs to one of the three already identified complementation qde groups (Cogoni and Macino 1997). The restoration of an al-1 silenced phenotype occurs in heterokaryons with qde-2 and qde-3 mutants. It is not possible to complement with qde-1 mutants (Table 1), indicating that the 107 strain is mutated at the qde-1 gene.

TABLE 1

The 107 strain is mutated at the qde-1 gene qde mutant strains used in specific heterokaryons

|     | 107 | M17 | M18 | M10 | M11 | M7  | M20 |
| --- | --- | --- | --- | --- | --- | --- | --- |
| 107 | WT  | AL  | AL  | AL  | AL  | WT  | WT  |
| M17 |     | WT  | WT  | AL  | AL  | AL  | AL  |
| M18 |     |     | WT  | AL  | AL  | AL  | AL  |
| M10 |     |     |     | WT  | WT  | AL  | AL  |
| M11 |     |     |     |     | WT  | AL  | AL  |
| M7  |     |     |     |     |     | WT  | WT  |
| M20 |     |     |     |     |     |     | WT  |

WT = heterocaryon with a wild type phenotype for carotenoid (bright orange);
AL = heterocaryon with an albino phenotype wherein the al-1 gene silencing is restored.

The qde mutant strains were described by Copgoni and Macino (1997); M17 and M18 are qde-3 mutants; M10 and M11 are qde-2 mutants; M7 and M20 are qde-1 mutants. The heterokaryon phenotypes were examined by visual inspection after a seven day growth in the presence of light.

In order to isolate the qde-1 gene, the "tagging" plasmid was recovered from the 107 strain by means of a procedure suitable for the liberation of the plasmid using the BglII restriction enzyme having a single restriction site within the tagging plasmid. The pCR4 plasmid was recovered after chromosomal DNA re-ligation following a BglII restriction (see FIG. 2a). The chromosomal DNA flanking the insertion site was isolated using the BglII and PstI enzymes and the resultant restriction fragment was used to probe a N. crassa genomic library in cosmids. Cosmids 58G11 and 40H7, both positively hybridizating, were introduced by means of an UV induced transforming experiment in the 107 strain and in the M7 qde-1 mutant strain. Both the cosmids were able to complement the two assayed qde-1 mutants. The restoration of the al-1 gene silencing which determines the appearance of a white phenotype indicates that both the cosmids contain a functional qde-1 gene. By using the same flanking DNA like a probe, two EcoRi fragments from 40H7 and 58G11, respectively having 7,9 and 10,0 kB, were identified and subcloned (see FIG. 2a). Both the EcoRi fragments (p79E and p10E plasmids) are able to complement the qde-1 strain (107 and M7) but not the qde-2 (M10) and qde-3 (M17) mutant strains (Table 2), indicating that the qde-1 functional gene is contained in the 7,9 Kp EcoRi fragment.

TABLE 2

Complementation with the qde-1 gene

| Plasmids | qde mutant strains used | | | |
| --- | --- | --- | --- | --- |
|  | 107 | M7(qde-1⁻) | M10(qde-2⁻) | M17(qde-3⁻) |
| P79E | 58/200(29%) | 48/200(24%) | 0/200(0%) | 0/200(0%) |
| P10E | 51/100(25%) | 25/100(25%) | 0/200(0%) | 0/200(0%) |
| PSX | 0/200(0%) | 0/200(0%) | — | — |
| PDX | 0/200(0%) | 0/200(0%) | 0/200(0%) | 0/200(0%) |

The complementation frequency is reported as percent of the transforming strains which show an albino phenotype with respect to the total number of transforming strains. The pMXY2 plasmid was used as negative control.

The ability of the qde-1 gene in restoring the al-1 gene silencing only in corresponding mutants, excludes the possibility that the DNA cloned fragment is able to restore the al-1 gene silencing, apart from the qde complementation group. In addition the M7 strain transformed with the 7,9 Kb EcoRI fragment allows the ability in silencing an other al-2 carotenogenic gene when introduced by transformation (not showed data). The 7,9 Kb EcoRI fragment was further cloned using the XbaI site (see FIG. 2a) which cuts the center the EcoRI fragment. Both the XbaI/EcoRI (pSX and pDX plasmids) fragments were not able to complement the 107 and M7 strains (see Table 2), suggesting that the XbaI site is probably localised within the qde-1 gene.

The whole region of the EcoRI fragment which includes the putative qde-1 gene and the adjacent regions were sequenced, revealing an open reading frame (ORF) of 4206 bp which encodes for a putative protein containing 1402 amino acids. Two different results suggest that this ORF corresponds to the qde-1 gene. Firstly the XbaI restriction site used to subclone the 7,9 Kb EcoRI fragment is localized in the center of the ORF (FIG. 2a) and therefore is consistent with the result that both the KbaI/EcoRI fragments are not able to complement the qde-1 mutation (Table 2). Secondly by means of Southern analysis (see FIG. 2b) the insertion site of the tagging plasmid in the 107 strain was mapped to be within the BglII and NaeI restriction sites in the ORF. No size variation of the flanking regions was detected, therefore excluding the possibility that the deletions include other ORFs within the 7,9 Kb EcoRi region. The cDNAs synthesized by inverted PCR (RT-PCR) revealed a co-linearity with the genomic DNA indicating that no intron is present. The expression of the qde-1 gene was analyzed by Northern analysis using a probe including the qde-1 ORF (FIG. 2a). Thus a transcript of about 5000 nt was detected and further it was found out that the qde-1 mRNA basal level in an al-1 silenced strain (6XW) was twice than in a not transformed WT strain (see FIG. 3). In addition the qde-1 whole length mRNA is not detectable in the qde-1 107 insertional mutant strain where, on the contrary, a smaller band is included suggesting that the qde-1 truncated transcripts are produced as the integration result. The fact that the qde-1 gene expression is specifically increased in a silenced strain suggests the existence of a regulatory mechanism able to activate cell components of the silencing machinery in the transgenic strains.

Figure 5:
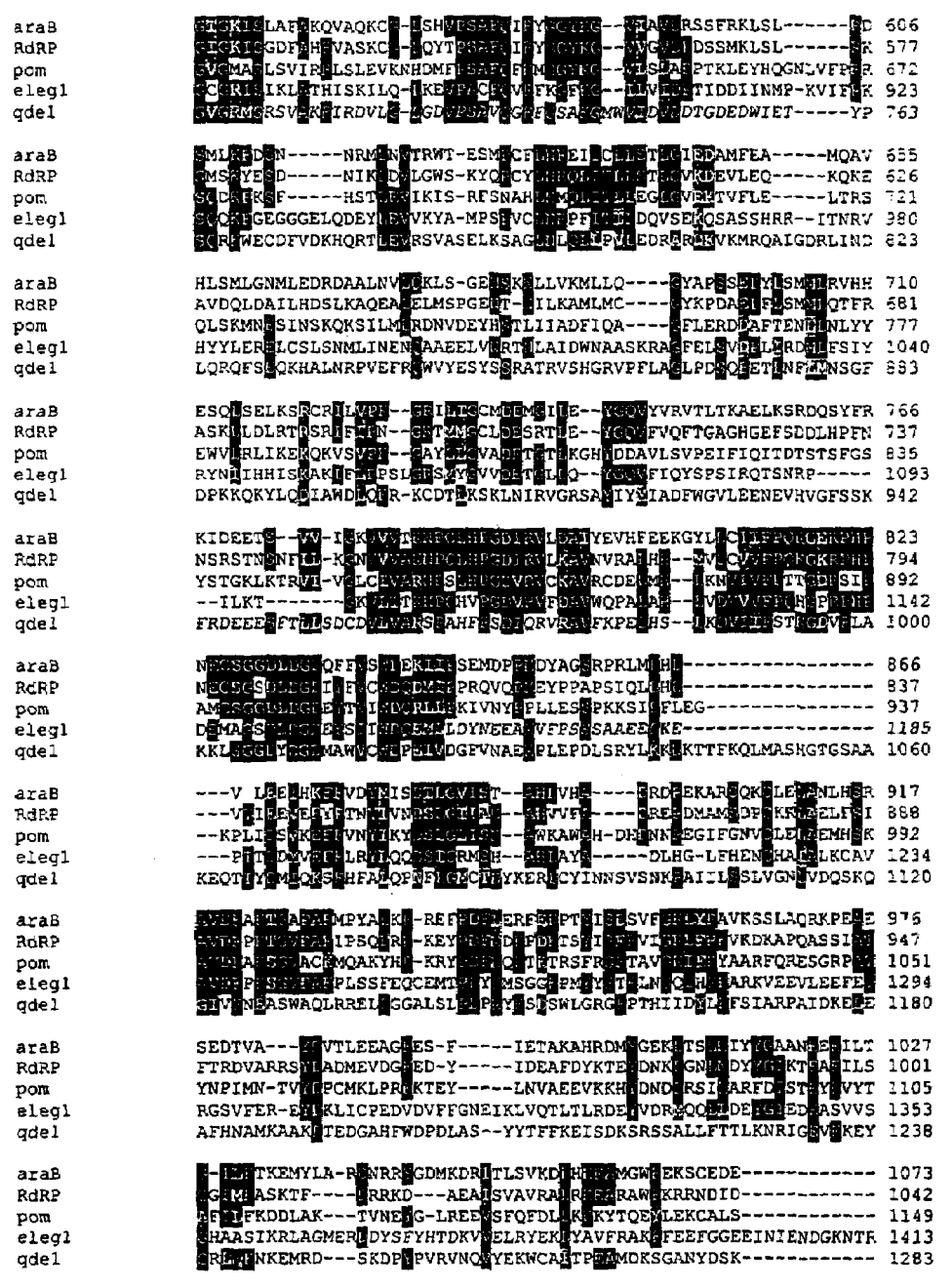

The QDE-1 protein deduced from the nucleotide sequence contains 1402 amino acids (see FIG. 4), the molecular weight and statistical pI thereof being 158.004 Da and 8.0, respectively. The QDE-1 protein does not contain a signal peptide or a transmembrane domain indicating that it is probably an intracellular protein. Furthermore the idiopathic plot suggests that QDE-1 is a soluble protein. A BLAST study showed that qde-1 has an homology statistically significant with hypothetical proteins from various other organisms comprising: two ORFs from *C. elegans* (Z4834 and Z78419 EMBL entry numbers) with expected values (E value) of 2e-16 and 9e-10, respectively, one ORF from *S. pombe* (Z98553 EMBL entry number) with an 3e-13 E value; four ORFs from *A. thaliana* (AF080120 and AC005169 EMBL entry numbers, the latter comprising thre ORFs at the same chromosomal localization,) and 8e-15, 7e-06, 4e-05, 5e-02 E values, respectively. Finally a significant homology (2e-17 E value) with a putative protein coded by tomato cDNA (Y10403 EMBL entry number) was discovered. The discovered homology does not extend over the whole protein but it is limited to a portion containing 570 amino acids, from aa. 710 to aa. 1282, which defines a conserved domain (see FIG. 5). Among the identified putative homologous proteins only that derived from the sequence of tomato cDNA was functionally characterized as a RNA-dependent RNA polymerase (RdRP, 9).

BIBLIOGRAPHY

Baulcombe, D. C. (1996) Plant Mol. Biol. 32, 79–88.
Cogoni, C. et al. (1996) EMBO J. 15, 3153–3163
Cogoni, C. and Macino, G. (1997) Proc. Natl. Acad. Sci. U.S.A. 94: 10223–10238.
Cabibbo, A. et al. (1991) Fungal Genetic Newsl., 38: 68–70.
Davis, R. H. and De Serres, F. J. (1970) Methods Enzymol. 17: 79–143.
de Carvalho Niebel, F. et al. (1995), Plant Cell 7:347–358.
Dehio, C., and Schell, J. (1994). Proc. Natl. Acad. Sci. U.S.A. 91: 5538–5542.
Dorer, D. R. and Henikoff, S. (1994). Cell, 77, 993–1002.
Elkind, Y. et al. (19990) Proc. Natl. Acad. Sci. U.S.A. 87: 9057–9061.
Flavell, R. B. (1994) Proc. Natl. Acad. Sci. U.S.A. 91: 3490–3496.
Garrick D., et al. (1998) Nature Genetics 18, 56–59.
Lindbo, J. A. et al. (1993) Plant Cell 5:1749–1759.
Maniatis, S. T. et al. (1982) Molecular Cloning—A Laboratory Manual, Cold Spring Harbor, N.Y.: Cold Spring Harbor Laboratory Press.
Mittelstein Scheid, O. et al. (1994) Mol. Gen. Genet. 244: 325–330.
Pal-Bhadra, M., et al., (1997). Cell 90, 479–490.
Palauqui, J. C. et al., (1997) EMBO J. 16: 4738–4745.
Pirrotta, V. (1997). TIG 13, 314–318.
Schiebel et al. (1998) The Plant Cell 10:2087–2101.
Schmidhauser, T. J. et al., Mol. Cell. Biol. 10: 5064–5070
Staben, C. et al. (1989) Fungal Genetics Newsl. 36:79–81.
Stam, M. et al. (1997) Plant Journal 1: 63–82.
van Blokland, R. et al. (1994), Plant, 6, 861–887.
Vaucheret, H. (1993), C. R. Acad. Sci. Paris, Sciences de la vie/Life sciences 316, 1471–1483.
Voellmer, L. J. and Yanofsky, C. (1987) Proc. Natl. Acad. Sci. USA 83, 4869–4873.
Wallrath, L. L. and Elgin, S. C. R. (1995). Genes & Development 9, 1263–1277.

The invention claimed is:

1. An isolated nucleotide sequence coding for a protein which has a gene silencing activity and comprises a RNA-dependent RNA polymerase domain, wherein said nucleotide sequence is the sequence from nt. 2447 to nt. 6652 of SEQ ID NO: 1.

2. An expression vector comprising, under the control of a promoter that directs the expression in bacteria, the nucleotide sequence according to claim 1.

3. An expression vector comprising, under the control of a promoter that directs the expression in plant organs, the nucleotide sequence according to claim 1 in a sense or anti-sense orientation.

4. An expression vector comprising, under the control of a promoter that directs the expression in fungi, the nucleotide sequence according to claim 1 in a sense or anti-sense orientation.

5. An expression vector comprising, under the control of a promoter that directs the expression in animals, the nucleotide sequence according to claim 1 in a sense or anti-sense orientation.

6. A Bacterial organism transformed the expression vector active in bacteria according to claim 2.

7. A Fungus transformed by the expression vector active in fungi according to claim 4.

* * * * *